US009907978B2

(12) United States Patent
Pankratov et al.

(10) Patent No.: US 9,907,978 B2
(45) Date of Patent: *Mar. 6, 2018

(54) SYSTEM FOR NON-INVASIVE HEART TREATMENT

(71) Applicant: CyberHeart, Inc., Mountain View, CA (US)

(72) Inventors: Michail Pankratov, Waltham, MA (US); Federico Benetti, Rosario (AR); Judie Vivian, Huntington Beach, CA (US)

(73) Assignee: CyberHeart, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/189,668

(22) Filed: Feb. 25, 2014

(65) Prior Publication Data

US 2016/0279442 A1    Sep. 29, 2016

Related U.S. Application Data

(63) Continuation of application No. 12/637,458, filed on Dec. 14, 2009, now Pat. No. 8,696,658, which is a continuation of application No. 11/080,318, filed on Mar. 14, 2005, now Pat. No. 7,645,276, which is a continuation of application No. 10/651,764, filed on Aug. 29, 2003, now Pat. No. 6,889,695.

(60) Provisional application No. 60/438,876, filed on Jan. 8, 2003, provisional application No. 60/445,716, filed on Feb. 7, 2003.

(51) Int. Cl.
*A61N 5/10* (2006.01)

(52) U.S. Cl.
CPC ............ *A61N 5/10* (2013.01); *A61N 5/1039* (2013.01); *A61N 5/1049* (2013.01); *A61N 5/1084* (2013.01); *A61N 5/1064* (2013.01)

(58) Field of Classification Search
CPC ...... A61N 5/10; A61N 5/1084; A61N 5/1049; A61N 5/1039; A61B 18/1492; A61B 18/04; A61B 18/14; A61B 2018/00577; A61B 2018/00357; A61B 2018/00351; A61B 2018/00392; A61L 318/1492; A61L 318/04; A61L 318/14
See application file for complete search history.

(56) References Cited

U.S. PATENT DOCUMENTS

| | | | | |
|---|---|---|---|---|
| 4,894,855 A * | 1/1990 | Kresse | ................... | A61B 6/032 378/189 |
| 6,778,850 B1 * | 8/2004 | Adler | ...................... | A61B 6/12 378/4 |
| 7,085,347 B2 * | 8/2006 | Mihara | .................... | A61N 5/10 378/197 |
| 7,182,725 B2 * | 2/2007 | Bonan | .................. | A61N 5/1002 600/3 |

(Continued)

*Primary Examiner* — Michael Peffley
(74) *Attorney, Agent, or Firm* — Wilson Sonsini Goodrich & Rosati

(57) ABSTRACT

The invention provides a non-invasive method for treatment of arrhythmia. In a first aspect, a method for treatment of atrial fibrillation in a heart of a patient comprises directing radiation from outside the patient toward one or more target treatment regions of the heart so as to inhibit the atrial fibrillation. The radiation may induce isolation of a pulmonary vein.

18 Claims, 5 Drawing Sheets

(56) References Cited

U.S. PATENT DOCUMENTS

2008/0177279 A1* 7/2008 Sumanaweera ........ A61B 34/20
606/130

* cited by examiner

SYSTEM FOR NON-INVASIVE HEART TREATMENT

CROSS-REFERENCES TO RELATED APPLICATIONS

The present application is a Continuation of U.S. Ser. No. 12/637,458 filed Dec. 14, 2009 (now U.S. Pat. No. 8,696,658); which application is a Continuation of U.S. Ser. No. 11/080,318 filed Mar. 14, 2005 (now U.S. Pat. No. 7,645,276); which application is a Continuation of Ser. No. 10/651,764 filed Aug. 29, 2003 (now U.S. Pat. No. 6,889,695); which claims the benefit of U.S. 60/438,876 filed Jan. 8, 2003 and 60/445,716 filed Feb. 7, 2003. The full disclosures, each of which are incorporated herein by reference in their entirety.

STATEMENT AS TO RIGHTS TO INVENTIONS MADE UNDER FEDERALLY SPONSORED RESEARCH OR DEVELOPMENT

Not Applicable

BACKGROUND OF THE INVENTION

The present invention is generally related to treatment of arrhythmia, and in one embodiment provides a non-invasive treatment of arrhythmia having long-term efficacy.

A typical adult human heart beats at a rate of about 70 beats per minute. The rate is not constant, however, and changes during and following exercise, with fear or anxiety, or for other reasons. A heart can also pump arrhythmically for many reasons, including damage to the heart's electrical conduction system. Arrhythmias interfere with the heart's ability to pump blood, and can result in severe symptoms, including death.

Atrial fibrillation is one of the most common cardiac arrhythmias. Atrial fibrillation occurs in as many 50% of patients undergoing cardiac operations. Patients with chronic Atrial Fibrillation may suffer from symptomatic tachycardia or low cardiac output, have a risk of thromboembolic complications, and are at risk for death. Until just a few years ago many health care providers thought atrial fibrillation to be a "nuisance" arrhythmia with few consequences. However, medical research has uncovered some devastating complications, including stroke, congestive heart failure, and cardiomyopathy. Many conditions have been associated with atrial fibrillation, including thyroid disorders, valve disease, hypertension, sick sinus syndrome, paricarditis, lung disease, and congenital heart defects. Atrial fibrillation can occur at any age, but its prevalence tends to increase with age and effects men slightly more often than women.

During Atrial Fibrillation, the atria lose their organized pumping action. In normal sinus rhythm, the atria contract, the valves open, and blood fills the ventricles (the lower chambers). The ventricles then contract to complete the organized cycle of each heart beat. Atrial fibrillation has been characterized as a storm of electrical energy that travels across the atria, causing these upper chambers of the heart to quiver or fibrillate. During Atrial Fibrillation, the blood is not able to empty efficiently from the atria into the ventricles with each heart beat. Blood can then pool and become stagnant in the atria, creating a site for blood clot formation. Such clot formation can become a primary source of stroke in patients with Atrial Fibrillation.

Non-surgical treatments are sometimes effective in treating atrial fibrillation. Several drugs are known, but may have significant side effects and are not ideal for treatment of acute fibrillation. Pharmacological therapies are also associated with adverse effects in a significant proportion of patients. Moreover, although electrical cardioversion (alone or in combination with anti-arrhythmic therapy) is often effective in restoring sinus rhythm, high recurrence rates of atrial fibrillation have been reported.

A number of invasive surgical procedures have been proposed for treatment of Atrial Fibrillation. Invasive procedures involving direct visualization of the tissues include the Maze procedure. Dr. James Cox and others proposed the original Cox-Maze procedure in which the atria are surgically dissected and then repaired. In the Maze procedure, for example, ectopic re-entry pathways of the atria are interrupted by the scar tissue formed using a scalpel or the like. The pattern of scar tissue prevented recirculating electrical signals which can result in atrial fibrillation.

The Maze surgical procedure has been simplified by the use of cryoprobes, radio frequency (RF) probes, and laser probes to effect the pattern of scar tissue. For example, ablation is sometimes used to terminate arrhythmias by introducing a catheter into the heart and directing energy at specific areas of heart tissue. By using a transarterial catheter to deliver the energy to the atria under fluoroscopy, interventional cardiologists have treated atrial fibrillation in a less-invasive manner. RF energy has been used successfully to terminate arrhythmias by introducing the catheter into the heart and directing the RF energy at specific areas of the heart tissue. Nonetheless, there is still a need for potentially non-invasive treatments of arrhythmia having long-term efficacy.

BRIEF SUMMARY OF THE INVENTION

The present invention provides non-invasive methods for treatment of arrhythmia.

In a first aspect, the invention provides a method for treatment of atrial fibrillation in a heart of a patient. The method comprises directing radiation from outside the patient toward one or more target treatment regions of the heart so as to inhibit the atrial fibrillation.

The radiation from outside the patient may induce isolation of a pulmonary vein, often effecting bilateral pulmonary vein isolation. In many embodiments, the radiation results in a formation of at least one lesion in the heart. The lesion can block conduction with or encircle the pulmonary vein, although a lesion maturation time may be present between directing of the radiation and isolation of the pulmonary vein. As atrial fibrillation often propagates from the pulmonary vein, the lesion can induce sufficient electrical isolation of the first pulmonary vein from adjacent electrical pathways of the heart such that the atrial fibrillation is inhibited. The radiation will often be directed to the target region(s) from a plurality of angles so as to avoid exceeding a tolerance of adjacent tissues.

At least one ectopic focus of the heart may be targeted for treatment with the radiation. The radiation may ablate linear lesions within the heart so as to inhibit an ectopic electrical pathway. The lesions may correspond to a Maze lesion pattern.

A first portion of the radiation may be directed to the patient in a first treatment, with a second portion of the radiation directed to the patient in a second treatment. Hence, the invention can accommodate fractionated radiation procedures for inhibition of Atrial Fibrillation. The patient may be assessed between the first and second treatments allowing the second treatment to be elected based on the assessment of the first treatment.

In many embodiments, the radiation can be delivered as a series of radiation beams extending toward the heart from different angles. The radiation beams may be dynamically registered with the one or more regions of the heart. The dynamic registration may be performed so as to compensate for pumping of the heart, and/or to compensate for movement of the patient and breathing. The radiation source may be moved around the patient by a robot arm, and the radiation may be directed toward the region of the heart from the radiation source along the series of radiation beams.

A plurality of target adjustment images may be acquired during the radiation treatment procedure. A position of the region(s) relative to a reference frame of the robot may be acquired from the target adjustment images. Radiopaque fiducial markers may be inserted to the patient around the region(s). The target images may be acquired with first and second fluoroscopic systems, and the target adjustment images may be acquired between delivery of successive radiation beams. The robot arm may move the source of radiation with six degrees of freedom.

The patient anatomy may be scanned so as to identify the target region(s), and the series of radiation beams may be planned, often before initiating treatment. Scanning the patient anatomy may comprise a Computer Tomography (CT) scan, a Magnetic Resonance Image (MRI) scan, sonography, or the like. Planning the series of radiation beams may comprise determining a number, intensity, and direction of the radiation beams. Planning of the target region may comprise determining a target region shape, with the radiation delivered so as to effect a non-isocentric treatment.

The radiation may be generated with a portable linear accelerator, the radiation often comprising x-ray radiation. Alternatively, the radiation may comprise gamma radiation. Other suitable types of radiation may also be employed, including various types of particle beams.

In another aspect, the invention provides a method for treatment of Atrial Fibrillation in a heart of patient. The method comprises directing a series of radiation beams from outside the patient and from different angles toward a target treatment region of the heart. The radiation beams are dynamically registered with the treatment region, and the irradiation of the target treatment region effects isolation of a first pulmonary vein so as to inhibit the Atrial Fibrillation.

DETAILED DESCRIPTION OF THE INVENTION

Radiosurgery is a known method of treating tumors in the body. The radiation can be delivered invasively in conjunction with traditional scalpel surgery, or through a percutaneous catheter. Radiation can also be delivered non-invasively from outside the body, through overlying tissue. Advances in stereotactic surgery have provided increased accuracy in registering the position of tissue targeted for treatment and a radiation source. For example, see U.S. Pat. Nos. 6,351,662 and 6,402,762. Stereotactic radiosurgery systems may be commercially available from ACCURAY, INC. of Sunnyvale, Calif., and BRAINLAB. The Accuray Cyberknife™ stereotactic radiosurgery system has reportedly been used to provide targeted, painless, and fast treatment of tumors.

Figure 1:
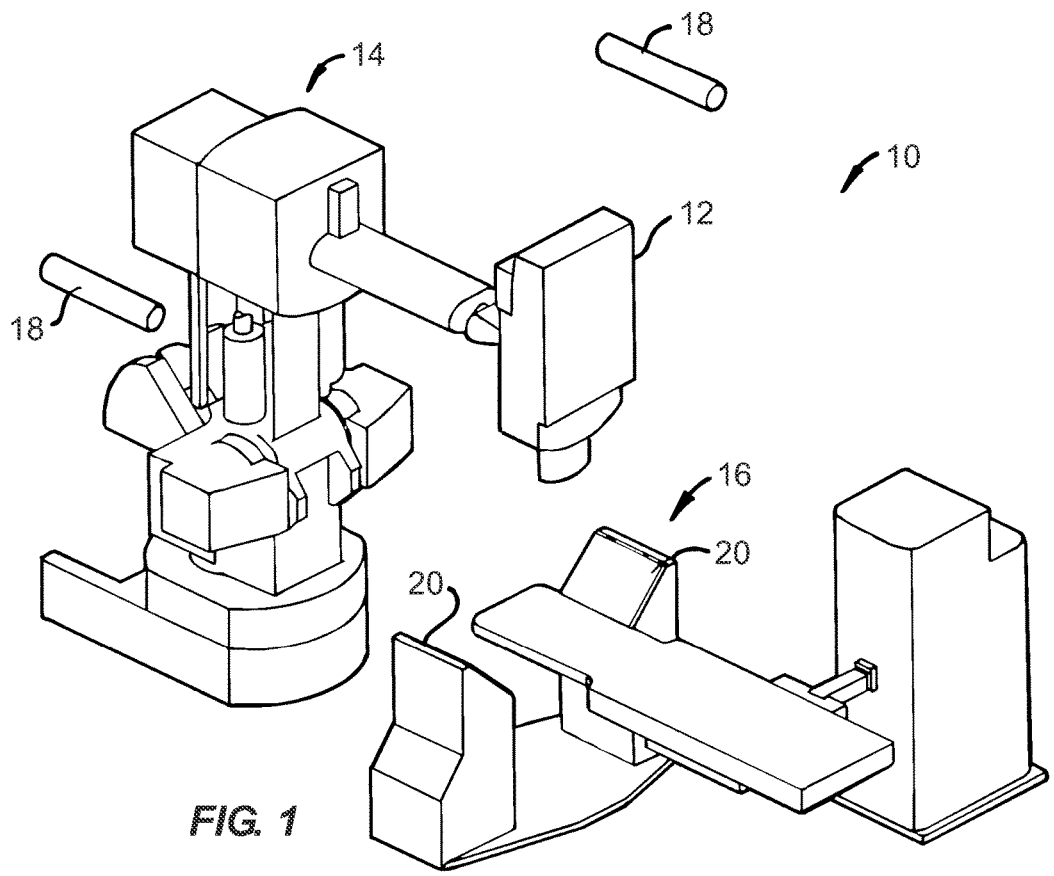
FIG. 1 is a perspective view of a radiation treatment system.

An exemplary Cyberknife stereotactic radiosurgery system 10 is illustrated in FIG. 1. Radiosurgery system 10 has a single source of radiation, which moves about relative to a patient. Radiosurgery system 10 includes a lightweight linear accelerator 12 mounted to a highly maneuverable robotic arm 14. An image guidance system 16 uses image registration techniques to determine the treatment site coordinates with respect to linear accelerator 12, and transmits the target coordinates to robot arm 14 which then directs a radiation beam to the treatment site. When the target moves, system 10 detects the change and corrects the beam pointing in near real-time. Near real-time image guidance may avoid any need for skeletal fixation to rigidly immobilize the target.

Improvements in imaging and computer technology have led to advances in radiation treatment, often for targeting tumors of the spine and brain. The introduction of CT scanners enables surgeons and radiation oncologist to better define the location and shape of a tumor. Further improvements in imaging technology include MRI and PET scanners. In addition, radiation therapy has also been aided by enhancements in ancillary technologies such as simulators to help position patients and advanced computers to improve treatment planning to enable the radiation oncologist to deliver radiation from a number of different angles. Computer technology has been introduced that enable radiation oncologists to link CT scanners to radiation therapy, making treatment more precise and treatment planning faster and more accurate, thereby making more complex plans available. Such advancements allow integrated conformal therapy, in which the radiation beam conforms to an actual shape of a tumor to minimize collateral damage to the surrounding healthy tissue. By combining simulators and imaging and treatment planning computers, the irradiation can be precisely administered.

System 10 makes use of robot arm 14 and linear accelerator 12 under computer control. Image guidance system 16 can monitor patient movement and automatically adjust system 10 to maintain radiation registration with the selected target tissue. Rather than make use of radiosurgery system 10 and related externally applied radiosurgical techniques to tumors of the spine and brain tissues, the invention applies system 10 to numerous cardiac conditions, and in one exemplary method to the treatment of Atrial Fibrillation.

Tradition radiosurgery instruments without image guidance technology rely on stereotactic metal frames screwed into the patient's skull to accurately target a tumor. Traditional radiosurgery has its drawbacks, the biggest of which relate to the use of the frame, including the pain and difficulty of accurately reattaching the frame in precisely the same location, along with the inability to target tissues other than those in the neck and head. Conventional linear accelerators for these systems can also be the size and weight of an automobile. Frame-based radiosurgery is generally limited to isocentric or spherical target treatments. To allow a device which can precisely pinpoint and treat tissues throughout the body, system 10 makes use of a portable linear accelerator, such as those originally designed for industrial inspections, which can be carried on a person's back. Linear accelerators may be commercially available from SCHONBERG RESEARCH GROUP, SIEMENS, PICKER INTERNATIONAL INC. or VARIAN.

System 10 allows intensity modulated radiation therapy. Using computerized planning and delivery, intensity modulated radiation therapy conforms the radiation to the shape of (for example) a tumor. By using computers to analyze the treatment planning options, multiple beams of radiation match the shape of the tumor. To allow radiosurgery, system 10 can apply intense doses of high-energy radiation to destroy tissue in a single treatment. Radiosurgery with system 10 uses precise spatial localization and large numbers of cross-fired radiation beams. Because of the high dosage of radiation being administered, such radiosurgery is generally more precise than other radiation treatments, with targeting accuracies of 1 to 2 mm.

Linear accelerator 12 is robotically controlled and delivers pin-point radiation to target regions throughout the body of the patient. Radiation may be administered by using a portable linear accelerator such as that illustrated in FIG. 1. Larger linear accelerators may also generate the radiation in some embodiments. Such linear accelerators may be mounted on a large rotating arm that travels around the patient, delivering radiation in constant arcs. This process delivers radiation to the target tissue and also irradiates a certain amount of surrounding tissue. As a result, such radiation therapy may be administered in a series of relatively small doses given daily over a period of several weeks, a process referred to as fractionation. Each radiation dose can create some collateral damage to the healthy surrounding tissue.

In the exemplary embodiment, robot arm 14 of system 10 is part of a pure robotics system, providing six degree of freedom range of motion. In use, the surgeon basically pushes a button and the non-invasive procedure is performed automatically with the image guidance system continuously checking and re-checking the position of the target tissue and the precision with which linear accelerator 12 is firing radiation at the tumor. Image guidance system 16 provides x-ray image guidance that gives the surgeon the position of internal organs and skeletal anatomy. Image guidance system 16 continuously checks, during a procedure, that the target is at the same place at the end of the treatment that it was at the beginning. The exemplary image guidance system included with the Accuray CyberKnife™ radiosurgery system takes the surgeon's hand out of the loop. The surgeon may not even be in the operating room with the patient. Instead, the image guidance system guides the procedure automatically on a real-time basis. By combining advanced image guidance and robotics, system 10 has proven effective in treating head and neck tumors without having to resort to stereotactic metal frame screwed into the skull of a patient.

Image guidance system 16 includes diagnostic x-ray sources 18 and image detectors 20, this imaging hardware comprising two fixed diagnostics fluoroscopes. These fluoroscopes provide a stationary frame of reference for locating the patient's anatomy, which, in turn, has a known relationship to the reference frame of robot arm 14 and linear accelerator 12. System 10 can determine the location of the skull or spine in the frame of reference of the radiation delivery system by comparing digitally reconstructed radiographs derived from the treatment planning images with radiographs acquired by the real-time imaging systems of the fluoroscopes.

Once the skeletal position is determined, the coordinates are relayed to robot arm 14, which adjusts the pointing of linear accelerator 12 and radiation is delivered. The speed of the imaging process allows the system to detect and adjust to changes in target position in less than one second. The linear accelerator is then moved to a new position and the process is repeated. Alternative systems may make use of laser triangulation, which refers to a method of using so-called laser tattoos to mark external points on the skin's surface so as to target the location of internal organs and critical structures. An alternative system commercialized by BRAINLAB uses a slightly different approach that measures chest wall movements.

The exemplary CyberKnife™ radiosurgery system is currently available for treatment of lesions throughout the cervical spine. These lesions may be benign or malignant, such as metastasis, meningiomas, and arterial venous malformations, the CyberKnife™ radiosurgery system has been used to successfully treat metastic lesions in patients who are otherwise not candidates for surgery or lesions which are not amenable to open techniques. Progress has also been reported in developing the CyberKnife™ radiosurgery system for use in the thoracic and lumbar regions as well, with preliminary experience being indicated as promising. System 10 combines robotics and advanced image-guidance to deliver true frameless radiosurgery. Multiple beams of image guided radiation are delivered by robot arm 14 mounted linear accelerator 12. The radiation can converge upon a tumor, destroying it while minimizing exposure to surrounding healthy tissue. Elimination of a stereotactic frame through the use of image guided robotics enables system 10 to treat targets located throughout the body, not just in the head. Radiosurgery is thus possible in areas such as the spine that have traditionally been difficult to treat in the past with radiosurgery, and for pediatric patients such as infants, whose skulls are too thin and fragile to undergo frame-based treatment.

System 10 allows ablation anywhere in the patient's body. The image-guidance system tracks bony landmarks of the skull to target radiation accurately. For body treatments, the image-guidance tracks small markers or fiducials percutaneously implanted in the tumor to target radiation. Advantages of system 10 include a treatment which can be provided on an outpatient basis, providing a painless option without the risk of complications associated with open surgery. Treatment may be applied in a single-fraction or hypo-fractionated radiosurgery (usually 2 to 5 fractions) for treatment near sensitive structures. System 10 provides flexibility in approach through computer control of flexible robotic arm 14 for access to hard-to-reach locations. System 10 also allows isocentric (for spherical) or non-isocentric (for irregularly shaped) treatments. Through the use of robotic arm 14, harm to the critical structures surrounding a lesion may be reduced. After careful planning, the precise robotic arm can stretch to hard-to-reach areas. The precise radiation delivered from the arm then minimizes the chance of injury to critical surrounding structures, with near-real-time image-guidance system 16 eliminating the need for rigid immobilization, allowing robot arm 12 to track the body throughout the treatment.

Figure 2:
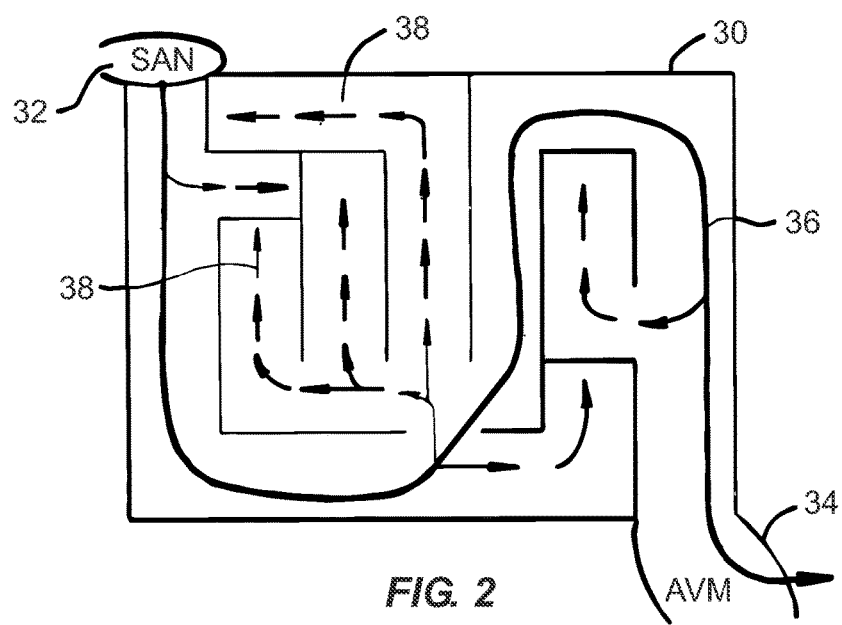
FIG. 2 is a schematic illustration of a simplified Maze lesion pattern.

Referring now to FIG. 2, Cox and his colleagues first described the Maze procedure for treatment of atrial fibrillation. In the original Maze procedure, ectopic re-entry pathways of the atria are interrupted by introducing scar tissue using a scalpel. In FIG. 2, a simple Maze path is conceptually illustrated. Maze lesion pattern 30 has one entrance 32, one exit 34, and one through path 36 with multiple blind alleys 38. Since the initial description of the Maze procedure by Cox and colleagues, a number of related open surgical approaches have been devised for the treatment of atrial fibrillation. Although successful in the irradication of atrial fibrillation in a high percentage of cases, these procedures are invasive, requiring median sternotomy, cardiopulmonary bypass, cardioplegic arrest, extensive cardiac dissection, and/or multiple atrial incisions. These procedures are also associated with significant morbidity. There are a number of iterations of the Cox procedure, including the Cox-Maze III procedure. While this operation has proven to be effective, it has significant shortcomings. The performance of the Cox-Maze III procedure requires cardiopulmonary bypass and an arrested heart. In most hands, it adds significantly to the cross-clamp time. Because of its perceived difficulty, few surgeons have learned to perform this operation. Finally, there is significant morbidity, particularly in terms of pacemaker requirements. These problems have led researchers to evaluate strategies to simplify the surgical treatment of atrial fibrillation.

It has been suggested that in many patients, atrial fibrillation may be caused by re-entry wavelets limited to specific areas near the origins of the pulmonary veins. Success has also been reported with more limited procedures aimed at electrical isolation with discreet atrial lesions, utilizing atriotomy, radiofrequency ablation, or cryoablation. As can be understood with reference to FIGS. 3A through 3D, alternative approaches have involved both investigating different lesion sets and using a variety of energy sources to create linear lesions of ablation to replace the more time-consuming surgical incisions. These newer procedures have the potential to decrease the procedure time by eliminating the extensive sewing associated with the many atrial incisions of the traditional Cox-Maze III procedure. A number of different technologies have been adopted to achieve this strategy. These include cryoablation, unipolar and bipolar RF energy, microwave energy, laser energy, and ultrasound. In general, the goals of atrial fibrillation ablation are to cure atrial fibrillation by creating linear lines of conduction block in the atria to replace the surgical incisions. These principally apply endocardial ablation in the beating heart, with most devices involving heating the tissue to cause coagulation necrosis.

Catheter-based atrial fibrillation ablation allows a less invasive approach, shortens operative time, and simplifies the operation. This reduces morbidity and mortality of the atrial fibrillation surgery, allowing for a more widespread application of these procedures. These operations decrease the invasiveness of the Cox-Maze III procedure, but in evaluating failures, it is often difficult to differentiate whether the lesion set was inadequate, or whether the technology was unable to create transmural lesions. Lesion patterns that have been studied in animal models include the original Maze III, the radial incisions approach, the tri-ring lesion pattern, and the Star procedure. Alternative patterns include simple bilateral pulmonary vein isolation, the Leipzig lesion pattern, and other patterns.

Figure 3A:
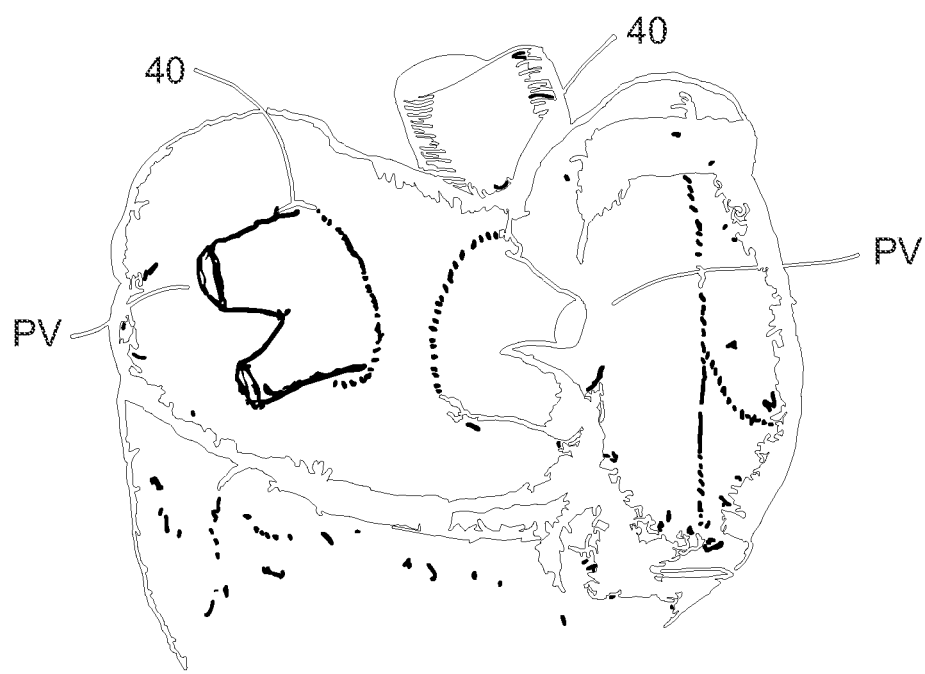
FIG. 3A-3D illustrate alternative patterns of lesions in the heart for treatment of arrhythmia.

Alternative ablation technologies may enable surgeons to more widely offer curative procedures for atrial fibrillation. Smaller lesion patterns can be developed from first principals or as a deconstruction of the Maze III or other more extensive pattern. It is possible that atrial fibrillation begins in most people as a disorder of the left atrium. Hence, lesions appropriate for paroxysmal atrial fibrillation (pulmonary vein isolation) could be given to patients with chronic atrial fibrillation to prevent recurrence. FIG. 3A illustrates lesions 40 effecting isolation of the pulmonary veins PV. These lesions abolish paroxysmal atrial fibrillation. The patterns mentioned above, except the Star procedure and the Leipzig lesion pattern isolate the pulmonary veins. Intraoperative measurements of pulmonary vein electrograms pre- and post-ablation to insure electrical silence of the muscle sleeves where triggers are thought to reside may confirm transmurality during application. Data suggests that in fifty percent of patients, effective therapy may be achieved by simply encircling the pulmonary veins with non-conductive lesions.

Lesion patterns may be tailored for the patient. For example, it has been shown that repetitive electrical activity originates in the left atrial appendage in patients with mitral valve disease. Electrical isolation of the left atrial appendage should be strongly considered in these patients. The tri-ring lesion pattern isolates the left atrial appendage, the pulmonary veins, and makes two connecting lesions. Atrial fibrillation associated with right atrial enlargement in congenital heart disease, or atrial flutter following right atrial incisions in congenital heart procedures do not imply the need for such lesions in the majority of patients undergoing atrial fibrillation ablation. The right atrium has a longer effective refractory period than the left atrium and in general sustains only longer re-entry circuits, the most common being the counterclockwise circuit of typical atrial flutter. This can be ablated by a transmural lesions connecting the tricuspid annulus to the IVC. Additional lesions connecting a lateral right atriotomy to the IVC or coronary sinus to the IVC may ablate an atypical right atrial flutter. In general, epicardial ablation may be safer than endocardial ablation because the energy source is directed into the atrial chamber rather than outward into adjacent mediastinal structures.

If bilateral pulmonary vein isolation is the irreducible component of surgical ablation, here is a possible schema for adding additional lesions for a particular patient:
1. If associated with mitral valve disease, include left atrial appendage isolation and left atrial appendage connecting lesion.
2. If known left atrial flutter (rare) include MV, TV, and LA appendage connecting lesions.
3. If known right atrial flutter, giant right atrium, or planned right atriotomy, include ablation lesions from TV to IVC; consider additional lesions from CS to IVC and from atriotomy to IVC.
4. If giant left atrium, consider LA reduction at time of procedure.

The legion pattern may be based on considerations of safety. There is no lesion pattern that is "best" for all patients, but the least complicated lesion pattern that is safe and easy to deliver and shown to be effective for a given population can be considered the best for those patients.

Figure 3B:
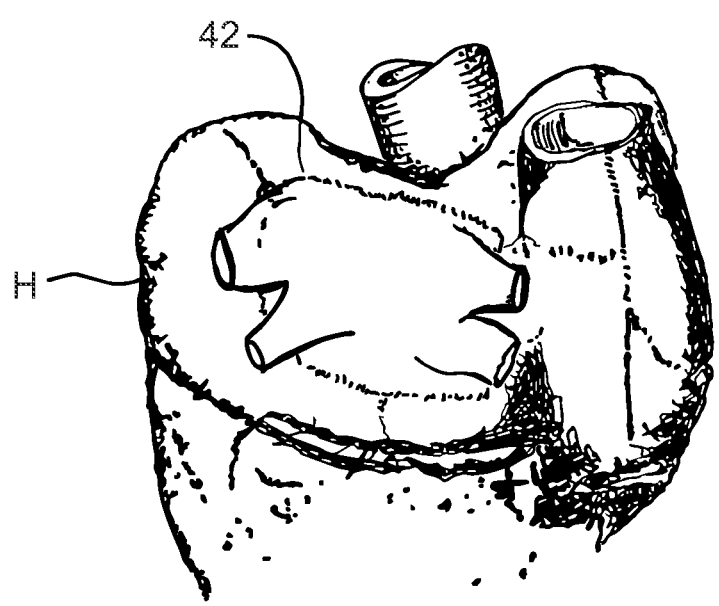
Figure 3C:
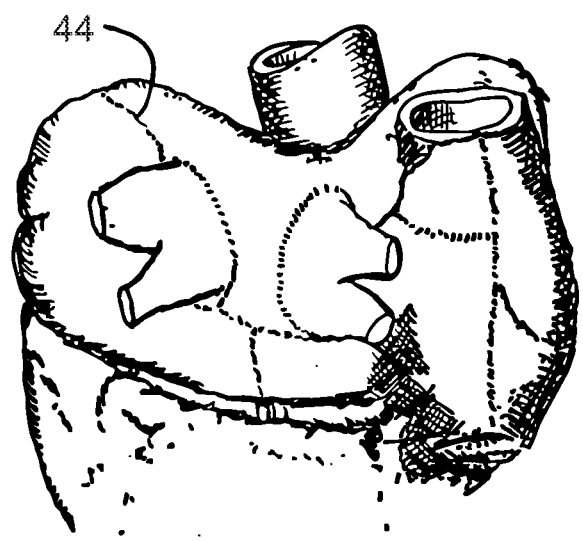
Figure 3D:
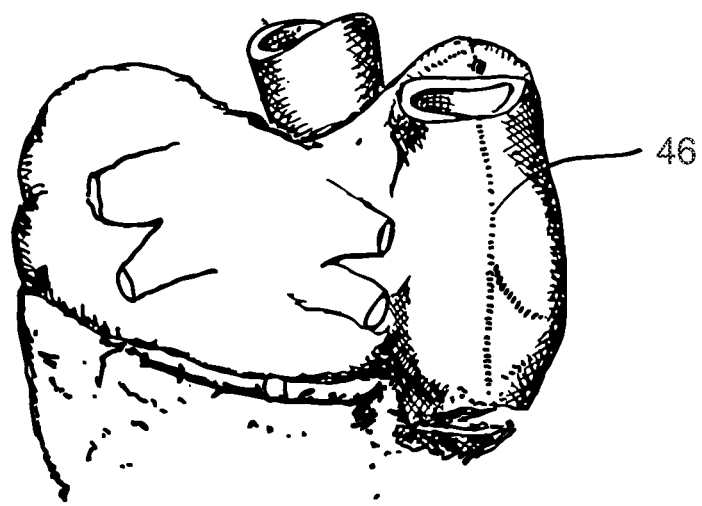

Referring now to FIG. 3B, a standard Maze III procedure has a lesion pattern 42 in heart H as illustrated. A modified Maze III procedure is illustrated in FIG. 3C, having a lesion pattern 44 applied in cryosurgical procedures. In FIG. 3D, a right atrial lesion 46 abolishes atrial flutter that occurs in the right atrium. However, most atrial flutter in the right atrium can be abolished by a single lesion in the isthmus below the OS of the coronary sinus.

Instead of cutting tissue using a Cox-Maze III, or other surgical procedure, and rather than invasive destruction of tissue using a cryoprobes or the like, radiosurgery system 10 (see FIG. 1) provides the ability to target specific foci, regions, lines, and so forth non-invasively. In a preferred embodiment, one could begin with the pulmonary veins, and then iteratively add additional lesions until atrial fibrillation is controlled. The exact doses of radiation will likely differ from patient to patient. A preferred basis for determining dosage is currently known treatment parameters used to produce lesions of similar tissues.

Vascular brachytherapy describes endovascular radiation therapy. Brachytherapy describes the application of radioactivity by a sealed source at a very short distance to the target tissue, e.g., by intracavity or interstitial source placement. The released energy during transformation of an unstable atom into a stable atom is absorbed in tissue. The quantity of absorbed in a tissue is the "dose" with the SI unit Gray (Gy=J/kg). The dose is strongly dependent on the type of radiation and the time span, also called "dwell time." An application dose rate is the dose of radiation per time (delivered or received). The dose rate delivered by a source depends on the activity of the source and the radionuclide that it contains. Biological effects of the absorbed radiation are dependent on the type of radiation and the type of tissue which is irradiated.

Gamma rays are photons originating from the nucleus of a radionuclide, which take the form of electromagnetic radiation. A heavy unstable nucleus will emit an alpha or beta particle followed by gamma radiation. Gamma rays penetrate deeply within tissues. X-ray radiation is comparable to gamma radiation. Its physical characteristics are similar, however, its origin is from the electron orbit. Beta radiation comprises beta particles, which are lightweight, high-energy electrons with either positive or negative charge. Beta particles can travel only finite distances within tissue, and when slowed by nuclei interactions they give rise to high penetration x-rays.

Absorbed radiation can cause damage in tissue either directly by ionization or indirectly by interacting with other molecules to produce free radicals which will subsequently damage the target. The target is often DNA, so that early and late toxic effects in normal tissue are mainly caused by cell death. Both total radiation dose and dose rate are important, since damage caused by radiation can be repaired between fractionated doses or during low dose rate exposure.

Human aortic cells show a significant decrease in their clonogenic potential after radiation. In injured vascular tissue, radiation doses of 12 to 20 Gy appear to efficacious in inhibiting neointimal formation. Possible high dose radiation effects include antiangiogenic effects and decreases of smooth muscle cells on the adventitia, selective inactivation of smooth muscle cells and myofibrolasts or complete elimination of their proliferative capacity at doses above 20 Gy. Lower dose radiation may promote cellular growth. Hence, promotion of vessel remodeling is dose dependent.

Figure 4:
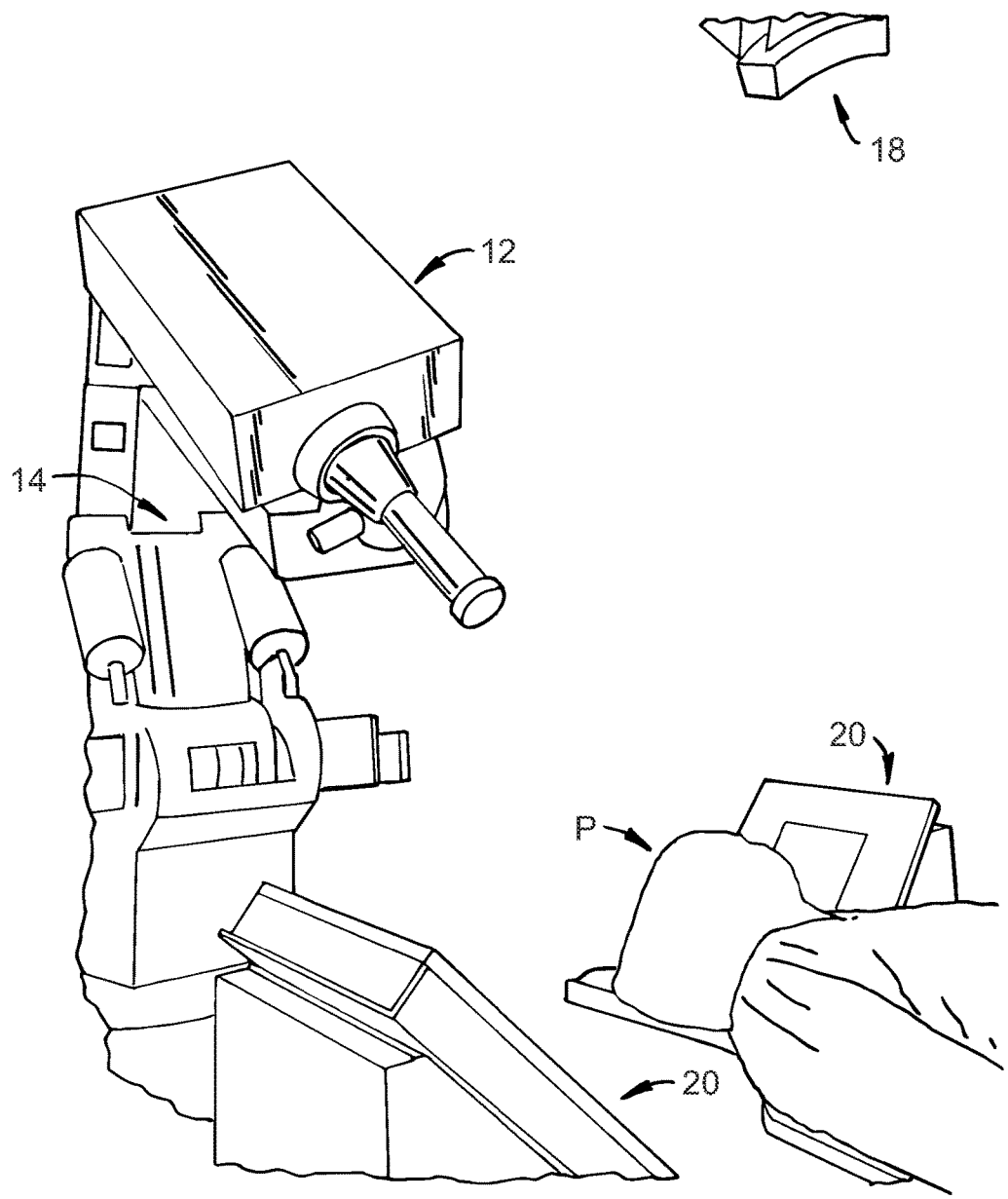
FIG. 4 illustrates stereotactic radiosurgery using the system of FIG. 1.
Figure 5:
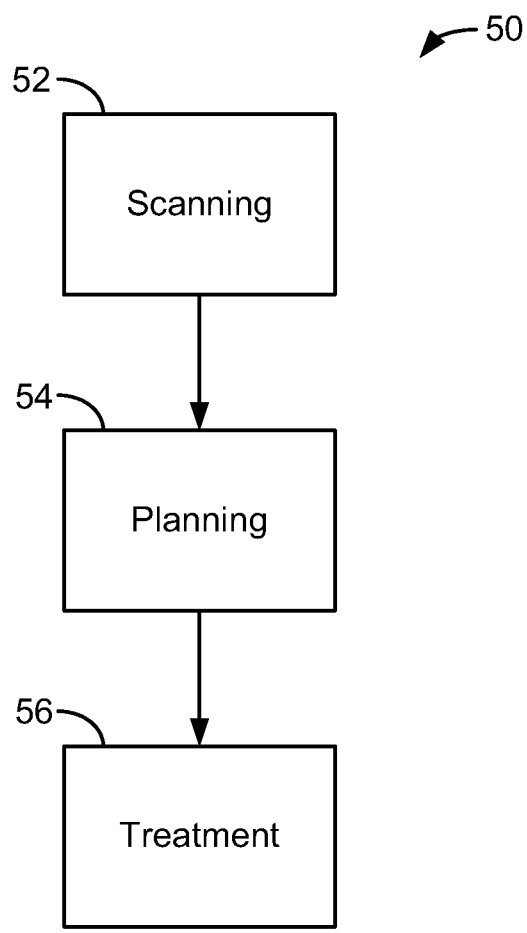
FIG. 5 is a flowchart schematically illustrating a radiosurgery treatment method.

A method for treating a target tissue can be understood with reference to FIGS. 4 and 5. Method 50 for using system 10 is basically a three-step outpatient procedure which consists of scanning 52, planning 54, and treatment 56. Treatment with system 10 begins as the patient undergoes a computer tomography (CT) or magnetic resonance imaging (MRI) as an outpatient. The process may begin with a standard resolution CT scan. MRI scans are optionally used for more accurate tissue differentiation. The patient usually leaves the hospital once the imaging is done. The scan is then digitally transferred to the system treatment planning workstation. Once the imaging is transferred to a workstation, the treatment plan is prescribed. A patient considered for system by treatment 10 may be assessed extensively by a team comprised of a treating neurosurgeon, radiation oncologist, and physicist to determine whether radiation is appropriate and how much. The patient may then undergo percutaneous placement of fiducials or small radiopaque markers that, in conjunction with high quality CT, provide three-dimensional stereotactic localization. The patient then returns several days later for the actual treatment.

On the CT scan, the surgeon and radiation oncologist identify the exact size, shape and location of the target and the surrounding vital structures to be avoided. Once the anatomy has been defined, the system software determines the number, intensity, and direction of radiation beams the robot will crossfire in order to insure that a sufficient dose is administered without exceeding the tolerance of the adjacent tissue. The beams are fired from multiple angles. While some of the radiation may hit surrounding tissues, there is a relatively steep dose gradient. System 10 is capable of treating regions larger than 3-4 cms in diameter. System 10 has been used with motion/respitory tracking software for treating liver and lung tumors where a patient's breathing could slightly distort the targeting of the tumor.

Sophisticated software allows for complex radiation dose planning in which critical structures are identified and protected from harmful levels of radiation dose. System 10 is capable of irradiating with millimeter accuracy. System 10 also has the ability to comprehensively treat multiple lesions. The patient may undergo open surgery and then radiosurgery of the non-operative lesions in one hospitalization.

As an example of the capability system 10, a 52 year old woman was diagnosed with renal cell carcinoma. She was diagnosed with a large metastatic lesion and received 3000 cGy external beam irradiation in 10 fraction. Her pain continued four months later, associated with a left radiculopathy. Radiosurgery with system 10 was recommended.

A large lesion was wedged between the patient's remaining left kidney and the previously irradiated spinal cord. Since the left kidney was her only remaining kidney, the dose was limited to 200 cGy to the kidney, and 300 cGy to the spinal cord. System 10's robotic capability maximized the dose to the tumor and spared the left kidney and spinal cord.

A 30-minute percutaneously fiducial placement procedure was performed one week prior to radiosurgery treatment. The patient was immobilized and a 30 mm collimator was used to treat with a single fraction to a prescribed dose of 1200 cGy that was calculated to the 80% isodose line. The maximum dosage was 1550 cGy, and the tumor volume was 31.3 cc's. Only 0.252 cc of the spinal cord received greater than 800 cGy.

Treatment was tolerated without difficulty or any discernable acute effects and lasted approximately 1 hour. No sedation was necessary and the patient went home that day. The patient reported a significant improvement in pain at her one-month follow-up.

In using system 10 to treat atrial fibrillation, the procedure is pre-planned using a 3D image (CAT, MRI, 3D Echo, etc.) of the patient to sequence the direction and intensity of the radiation to cause the clinical effect precisely in the targeted cells with minimal effect to the surrounding healthy tissue. The typical application relies upon additive effective up to 50 or more passes at a target, directed from different directions so that the more superficial and deeper tissues around the target receive much lower doses. The accumulative effect of the multiple passes may be immediately ablative, or may be sufficient only to provide coagulation and longer term necrosis.

Advantages of the inventive approach over surgical intervention should be immediately apparent. Surgical approaches are necessarily invasive, and are associated with significant morbidity. The distinction applies to even more limited surgical procedures for electrical isolation of discreet atrial regions, including for example, atriotomy, RF ablation, and cryoablation. The inventive subject matter discussed herein provides ways to perform the ablation of ectopic pathways using focused, image-guided, completely non-invasive methods for energy delivery, effecting a complete treatment without the need for surgery or a percutaneous procedure. The procedure may be offered as an iterative treatment permitting minimal treatment, until the desired clinical result is attained. The procedure, being non-invasive, can be offered as an outpatient procedure without the associated need for an anesthetic or pain medication. Patients needing mitral valve repair concomitantly with atrial fibrillation therapy will likely be an early subset due to the potential of fiducial marker placement at the time of the valve intervention.

As illustrated in FIG. 4, during a procedure with system 10, a patient P lies still on a treatment table. Generally no sedation or anesthesia is used because the treatment is painless, and the procedure can last anywhere from between 30 to 90 minutes depending on the complexity of the case and the dose to be delivered. The treatment itself involves the administration of numerous radiation beams delivered from different directions, typically in 10 to 15 second bursts. Prior to the delivery of each radiation beam, a stereo pair of x-ray images is taken by image guidance system 16 (see FIG. 1) and compared to the original CT scan (or the like). Between each dose, system 10 uses the information relayed from image-guidance system 16 to adjust robotic arm 14 to the movement of the target, which can be caused by anything from blood flow to the patient breathing. The patient normally leaves the hospital immediately after the treatment is completed, and follow-up imaging is generally preformed to confirm the treatment. System 10 can administer fractionated radiation therapy over the course of several days. Most patients only need one treatment, although some will require treatment with several sessions over several days.

Image-guidance technology is of interest for externally applied radiosurgical techniques to treat cardiac disease. Applicable image-guidance technologies will improve the accuracy of targeting. Dynamic registration of the patient can account for patient movement, even movement of the heart during pumping and breathing.

Advantageously, the novel treatments described herein can be iterative. Rather than target many foci or regions as is often done in an invasive procedure, externally applied radiosurgical techniques can address one or more focus or regions on one day, and the then other foci or regions on another day as needed. The interim period between treatments can be used to access the need for subsequent treatments. Such iterative or fractionated treatment is thus more conservative than current methods.

Suitable types of radiation, including particle beam radiation, may be employed. For example, the present invention encompasses the use of a GammaKnife™ radiosurgery system to ablate ectopic pathways in the atria. Although gamma radiation could be administered during open heart or other invasive procedures, the currently preferred applications are substantially non-surgical.

All suitable radiosurgery system are contemplated with the energy source, duration and other parameters varying according to a size of the patient and other factors. A typical GammaKnife™ radiosurgery system may contain (for example) at least about 200 cobalt-60 sources of approximately 30 curies each, all of which are placed in an array under a heavily shielded unit. The shielded unit preferably comprises lead or other heavy metals.

Gamma radiation may be directed to specific target points at a center of radiation focus. Radiation may be provided during one or more treatment sessions. For example, a dose of 5000 cGy could be delivered within 20 minutes to an effected area defined previously by computer tomography (CT), magnetic resonance imaging (MRI), or angiography.

An image-guided version of a gamma radiation radiosurgery system may also be useful. For example, a camera and/or light or other photo device may be coupled to a portion of the contemplated gamma radiation radiosurgery system. The heart may be beating during the procedure.

While the exemplary embodiments have been described in some detail, by way of example and for clarity of understanding, those of skill in the art will recognize that a variety of modification, adaptations, and changes may be employed. For example, multiple energy sources may be employed, including laser or other photoenergy sources, in combination with one or more forms of radiation. Hence, the scope of the present invention may be limited solely by the appending claims.

What is claimed is:

1. A system for treatment of atrial fibrillation in a heart of a patient, the system comprising:
   a source of particle beam radiation or x-ray radiation; and
   a system comprising a computer processor having a means for treating atrial fibrillation by directing the particle beam radiation or x-ray radiation from outside the patient toward one or more target treatment regions in the heart of the patient so as to inhibit the atrial fibrillation, the system coupled to the source of particle beam radiation or x-ray radiation.

2. The system of claim 1, further comprising computer software defining a planned plurality of radiation beams for transmission relative to a planning image of the heart so as to induce an arrhythmia-inhibiting lesion pattern, the computer software coupled to the computer processor.

3. The system of claim 2, further comprising a tomography or magnetic resonance imaging system for acquiring the planning image of the heart, the imaging system to the computer processor.

4. The system of claim 1, further comprising a registration imaging system coupled to the computer processor so that the computer processor dynamically registers the planned plurality of radiation beams with one or more target treatment regions of the heart of the patient during treatment.

5. The system of claim 1, further comprising a robot supporting the source of particle beam radiation or x-ray radiation, the robot moving the source of particle beam radiation or x-ray radiation relative to the patient so as to orient the particle beam radiation or x-ray radiation toward the heart of the patient per the planned plurality of radiation.

6. The system of claim 2, wherein the planned plurality of radiation beams defined by the computer software are configured to converge on the one or more target treatment regions in the heart of the patient.

7. The system of claim 6, wherein the planned plurality of radiation beams defined by the computer software are configured to ablate linear lesions within the heart sufficient to inhibit an electrical pathway.

8. The system of claim 7, wherein the linear lesions correspond to a Maze lesion pattern.

9. The system of claim 2, wherein the planned plurality of radiation beam are configured to effect bilateral pulmonary vein isolation.

10. The system of claim 2, wherein the planned plurality of radiation beams are configured to target at least one ectopic focus of the heart.

11. The system of claim 2, wherein the planned plurality of radiation beams defined by the computer software are configured to avoid exceeding a tolerance of an identified tissue structure adjacent to the one or more target regions.

12. The system of claim 2, wherein the planned plurality of radiation beams defined by the computer software comprise a number, intensity, and direction of the planned plurality of radiation beams.

13. The system of claim 1, wherein the source of particle beam radiation or x-ray radiation comprises a plurality of gamma radiation sources that emit gamma radiation directed at target points at a center of radiation focus.

14. The system of claim 13, wherein the plurality of gamma radiation sources are included in a shielded array unit.

15. The system of claim 2, wherein the source of— particle beam radiation or x-ray radiation comprises a linear accelerator mounted to a maneuverable robotic arm having at least six degrees of freedom.

16. The system of claim 15, wherein the computer processor further comprises an image guidance system comprising two fixed diagnostics fluoroscopes to provide a stationary frame of reference for locating the heart of the patient relative to the robotic arm and the linear accelerator.

17. The system of claim 1, wherein the source of particle beam radiation or x-ray radiation is included in a stereotactic system.

18. The system of claim 3, further comprising a display configured to output the planning image of the heart designating a three-dimensional location of the one or more target treatment regions in the heart of the patient.

* * * * *